United States Patent [19]
Karagueuzian et al.

[11] Patent Number: 5,817,132
[45] Date of Patent: Oct. 6, 1998

[54] DEFIBRILLATION APPARATUS AND METHOD

[75] Inventors: Hrayr S. Karagueuzian, Studio City; Peng-Sheng Chen, La Canada, both of Calif.

[73] Assignee: Cedars-Sinai Medical Center, Los Angeles, Calif.

[21] Appl. No.: 854,217

[22] Filed: May 9, 1997

[51] Int. Cl.$^6$ .................................................. A61N 1/39
[52] U.S. Cl. ......................................................... 607/5
[58] Field of Search ........................... 607/5, 6; 600/518

[56] References Cited

U.S. PATENT DOCUMENTS

| | | | |
|---|---|---|---|
| 5,366,487 | 11/1994 | Adams et al. | 607/5 |
| 5,447,520 | 9/1995 | Spano et al. | 607/5 |
| 5,471,991 | 12/1995 | Shinwar | 600/518 |

*Primary Examiner*—William E. Kamm
*Attorney, Agent, or Firm*—Pretty, Schroeder & Poplawski

[57] ABSTRACT

An implanted defibrillator continuously monitors a patient's heart to detect the presence of fibrillation and repeatedly, automatically computes the approximate entropy of a series of data representing the fibrillating heart at a moment in time. The first approximate entropy score that meets a predetermined relation with respect to a predetermined threshold value activates an energy delivery system to defibrillate the heart with a low level shock. The process continues until defibrillation is successful. An external defibrillator incorporates the approximate entropy algorithm to achieve low level defibrillation. A method is disclosed which times the delivery of a defibrillating shock to a fibrillating heart to coincide with the moment that the defibrillation threshold is at a minimum.

38 Claims, 4 Drawing Sheets

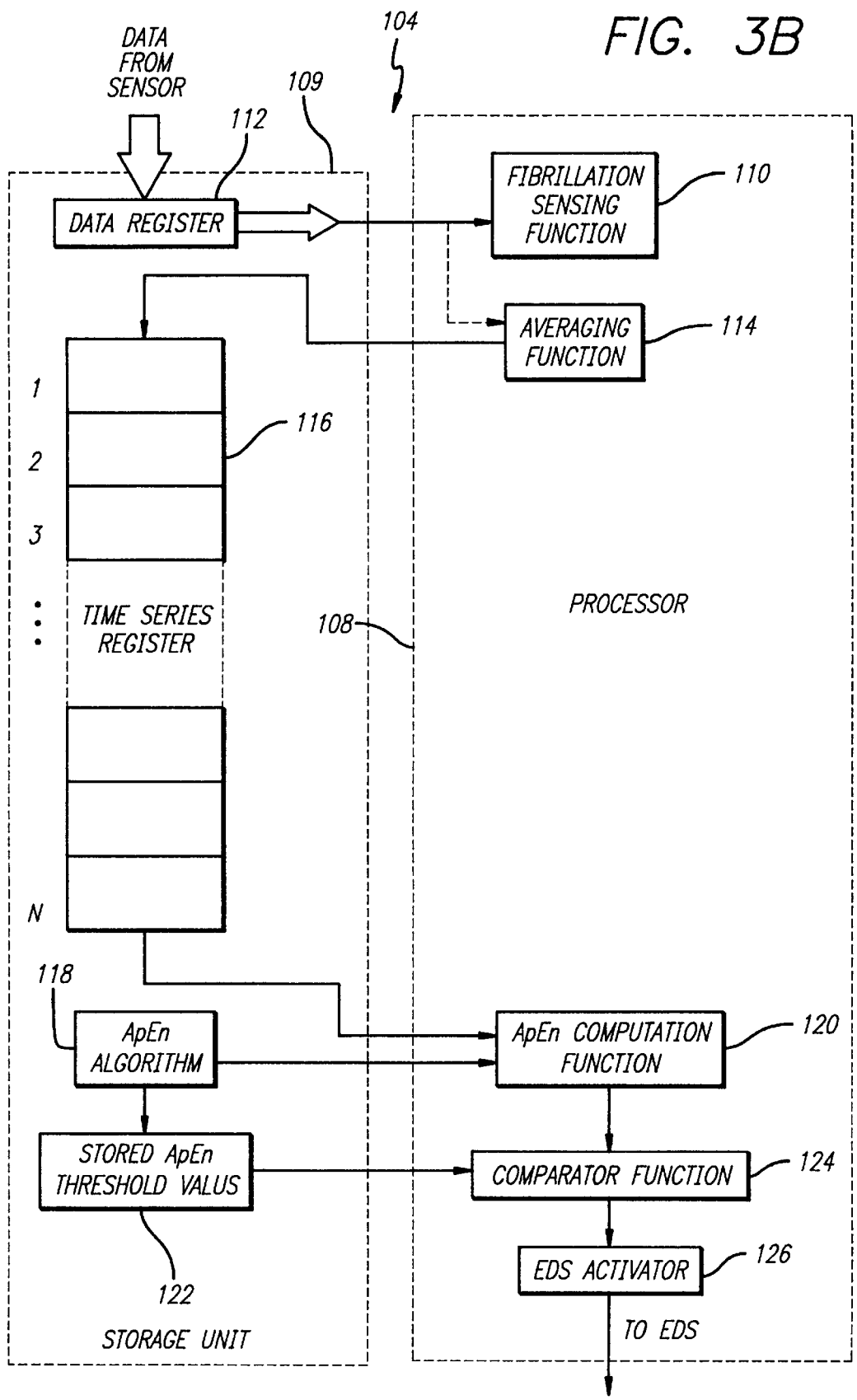

DEFIBRILLATION APPARATUS AND METHOD

BACKGROUND OF THE INVENTION

1. Field of the Invention

This invention relates generally to the treatment of heart failures and disorders and, more particularly, to apparatus and methods for defibrillating the heart through selective application of energy to the heart.

2. Description of the Related Art

Individuals that have congenital heart disease, particularly, an arrhythmia, or who have previously suffered one or more episodes of heart failure or heart disorder, are at a significantly higher risk than the general population of experiencing a future episode of heart failure or heart disorder. Two well known types of arrhythmias that afflict individuals are ventricular fibrillation ("VF") and atrial fibrillation ("AF"). VF constitutes the primary mechanism seen in sudden cardiac arrest and is manifested by the absence of organized electrical activity and synchronized mechanical pumping. AF is manifested by the extremely rapid contractions of the atria. Both arrhythmias are serious heart disorders but VF is particularly lethal if not quickly treated.

Electrical defibrillation is a known method for bringing a patient out of VF or AF. It typically entails the application of an electric shock of substantial energy, e.g. 10–30 joules or more, across a portion of the myocardium in order to depolarize the ventricle or atrium and to return organized, sinus rhythm to the heart. Multiple shocks are often required. Originally, restoring normal heart function to these patients could be accomplished only with external defibrillation treatment at a hospital, in an ambulance, or other medical care facility. This treatment involved the placement and activation of paddles connected to an electric shock apparatus on the patient's thorax. Thereafter, the advent of the automatic, surgically-implanted cardioverter defibrillator ("AICD" or "ICD") permitted VF and AF treatment outside a hospital, ambulance, or other medical care facility. Typically, upon sensing an occurrence of VF or AF, an ICD automatically applies one or more defibrillating shocks to the heart until normal sinus rhythm is restored.

FIG. 1 depicts a representative example of a conventional ICD 20 implanted in the subclavian area 8 of a patient 10 for the purpose of defibrillating the patient's heart 12. The ICD 20 includes an enclosed control box, or enclosure 22 that houses a processor 24 and a shock or pulse generator 26. The size of the control box is relatively large when compared to a conventional pacemaker. For example, the Ventritex "V-145D" ICD has a volume of 57 cc and weighs 109 grams; CPI's "Mini II Model 1762" has a volume of 59 cc and weighs 115 grams; and the Medtronic "Micro Jewel 7221 Cx" has a volume of 72 cc and weighs 116 grams. The conventional pacemaker, on the other hand, has a volume considerably less than 50 cc. The largest component in the control box is the energy-storing capacitor 27 of the shock generator capable of providing a shock of 30 or more joules. Its relatively large size is the primary limitation in development efforts to further downsize ICD's.

In order to accomplish appropriate defibrillation, a sensing/energy delivery electrode 28 is placed endocardially within a ventricle of the heart 12. The electrode senses ventricular rate and transmits, through a subcutaneous rate sensing lead 30, information reflective of this rate to the processor located in the control box. Additionally, the electrode is connected to the shock generator 26 in the control box 22 for delivering shocks to the heart.

In operation, when the heart 12 starts to fibrillate, the electrode 28 provides information to the processor which, in turn, activates the shock generator 26. The capacitor 27 is charged and delivers an electric shock to the heart electrode. If the processor determines that the heart is no longer fibrillating, it deactivates the shock generator 26, thereby signifying successful defibrillation. However, if the processor determines that the heart is still in fibrillation, it reactivates the shock generator so as to recharge the capacitor via a battery (not shown) to thereby cause the generator 26 to deliver another shock to the heart 12. This process continues for a preset number of times until either the heart is successfully converted out of fibrillation, or some preset limit is reached (such as 5 consecutive unsuccessful shocks).

FIG. 2 shows a representative example of a conventional external defibrillator 60 functioning on a patient 50 lying in the prone position, on a bed in an emergency room. Typically, an ECG (not shown) is connected to the patient to monitor the heart activity. The defibrillator 60 is powered by AC wall power 70 which is converted internally to DC power. The operator manually sets the energy level to be delivered to the patient via an output controller 76 and depresses a button 78 to activate the defibrillator. Therapy leads 72 transmit the energy to a pair of therapy paddles 74 which are placed on the chest 52 of the patient 50 for defibrillation.

Conventional ICD's do have advantages. For one, they tend to reduce the risk of sudden death or serious injury from arrhythmias. Thus, they have had the capacity to dramatically increase the life expectancy of patients within whom they are implanted. Nevertheless, ICD's have not gained as widespread acceptance as might have been expected. A primary reason is that after the fibrillation is sensed an ICD needs to deliver a shock of a relatively strong intensity in order to successfully defibrillate the heart. This requirement has a number of drawbacks. First, these powerful shocks, which sometimes reach thirty joules or more, can cause severe discomfort and undue pain to the patient. Consequently, many candidates for ICD's are simply not prepared to endure the dreaded defibrillating shock, as well as the psychological uneasiness or fear accompanying the knowledge that a shock may occur at any time. Thus, they refuse to have a given ICD implanted. Others have fainted from the magnitude of the defibrillating shocks, thereby causing additional health and safety concerns. As is conventionally understood, the discomfort and pain caused by the required shock is equally present with external defibrillation.

Second, to successfully deliver the requisite shock in a portable, battery-operated ICD device, a relatively large energy-storing capacitor needs to be employed. This constraint tends to severely limit the ability of ICD manufacturers to downsize these rather large devices.

A third problem is that the relatively high energy requirement of the ICD tends to compromise the life of its battery, which is used to repetitively charge the capacitor. This is a substantial drawback because access to the surgically-implanted ICD for the purpose of battery replacement necessitates another invasive operation on an already sick patient.

Various efforts to address the aforementioned problems have been undertaken. Some of these efforts have centered on miniaturizing the energy-storing capacitors. Other efforts have focused on reducing the minimum amount of energy needed to successfully convert VF to normal sinus rhythm, known as the defibrillation threshold. These efforts primarily involve varying the shock waveforms. For example, one approach is to change the shock delivery from a monophasic waveform to a biphasic (bidirectional) waveform. Another is to change the shape, or "tilt," of the biphasic current delivery over time. Still another approach is the delivery of pulses simultaneously over two current pathways. However, to date, each of these efforts have only modestly reduced the required conversion energy. Above all cardiac defibrillation algorithms employed in defibrillators do not adequately take into account the underlying mechanisms of fibrillation.

Additionally, conventional defibrillators work on the theory that the abnormal activation patterns in a fibrillating heart takes a completely random and unintelligible form. Consequently, defibrillation research has focused on (1) identifying the existence of fibrillation, and then (2) generating and applying various types of pulses (shocks) to the heart to terminate it. While such efforts are commendable, they have not been adequately dispensed toward effectively addressing the above problems.

Accordingly, it should be appreciated that there exists a definite need for a defibrillation apparatus and method that can successfully defibrillate a heart in VF or AF with much lower energy levels than can be presently achieved. There also exists a definite need for a defibrillator which is smaller and lighter than existing devices. Further, there is a definite need for a defibrillation method, manifested in either an ICD or external defibrillator, which tends to more successfully defibrillate a patient and at the same time to minimize the pain perceived by the patient.

SUMMARY

The present invention, which addresses these needs, is embodied in an apparatus and method which tends to reduce the amount of energy that would otherwise be necessary to defibrillate a heart by selectively providing the energy to the heart based upon the approximate entropy ("ApEn") of the heart. When the ApEn of a given heart has a predetermined relation with respect to a preset value, defibrillation can be advantageously achieved at a reduced energy level. In one application, this level is less than 5 joules; in another it is less than 10 joules.

In particular, the apparatus includes an energy delivery system for delivering to a heart an electric shock of a predetermined energy level and a controller that receives data indicative of the rhythm of the heart and that selectively activates the energy delivery system in response to an approximate entropy score derived by the controller from the data. The invention has utility for improved defibrillation of a fibrillating ventricle or atrium of the heart. Further, the invention is embodied in both an implantable defibrillator and external defibrillator.

In another aspect of the invention, the apparatus includes a sensor, which is associated with the heart and is configured to detect a heart rhythm and transmit data indicative of the rhythm, an energy delivery system associated with the heart for delivery to the heart an electric shock of a predetermined energy level, and a controller responsive to the sensor that selectively activates the energy delivery system in response to an approximate entropy score derived by the controller from the data. Further, the apparatus may include multiple sensors or one sensor having multiple sensing poles. Moreover, the energy delivery system has an electric shock generator and at least one therapy lead associated with the heart. The sensor or sensors and the therapy lead or leads can also be integral with one another.

In a more detailed feature of the invention, the controller includes sensor data and approximate entropy processors that together cooperate with a comparator so as to permit an energy delivery system actuator to activate the energy delivery system. Specifically, the data processor receives heart data and repeatedly computes a plurality of data points substantially equally spaced in time. The approximate entropy processor then receives the data points and repeatedly computes an ApEn score from the data points. The comparator then compares the ApEn score to at least one preset ApEn threshold value stored in a memory of the controller, and provides output that is monitored by the energy delivery system activator to monitor the output of the comparator. In monitoring the output of the comparator, the activator activates the energy delivery system when the ApEn score has at least one predetermined relation with respect to the at least one preset ApEn threshold value, thereby defibrillating the heart.

In another more detailed feature of the invention, the controller repeatedly computes from the sensor data a scalar times series which is comprised of discrete data point equally-spaced in time. The controller then derives the ApEn score from the scalar time series. The ApEn score is defined by the equation:

$$ApEn(m,r,N) = \phi^m(r) - \phi^{m+1}(r)$$

and ranges from 0 to 2. The controller compares the ApEn score to a first preset approximate entropy threshold value stored in a memory of the controller, and then selectively activates the energy delivery system when the ApEn score has a predetermined relation with respect to a first preset approximate entropy threshold value. In one application, this predetermined relation arises when the ApEn score is less than the first preset ApEn threshold value. In another application, this relation arises when the ApEn score is greater than the first preset ApEn threshold value. In yet another application, this predetermined relation arises when the ApEn is either less than the first preset threshold value or greater than a second preset threshold value.

Other features and advantages of the present invention should become more apparent from the following description of the preferred embodiments, taken in conjunction with the accompanying drawings, which illustrate, by way of example, the principles of the invention.

BRIEF DESCRIPTION OF THE DRAWINGS

FIG. 3b is a block diagram of the controller of the defibrillator shown in FIG. 3a.

DETAILED DESCRIPTION OF THE PREFERRED EMBODIMENTS

Figure 1:
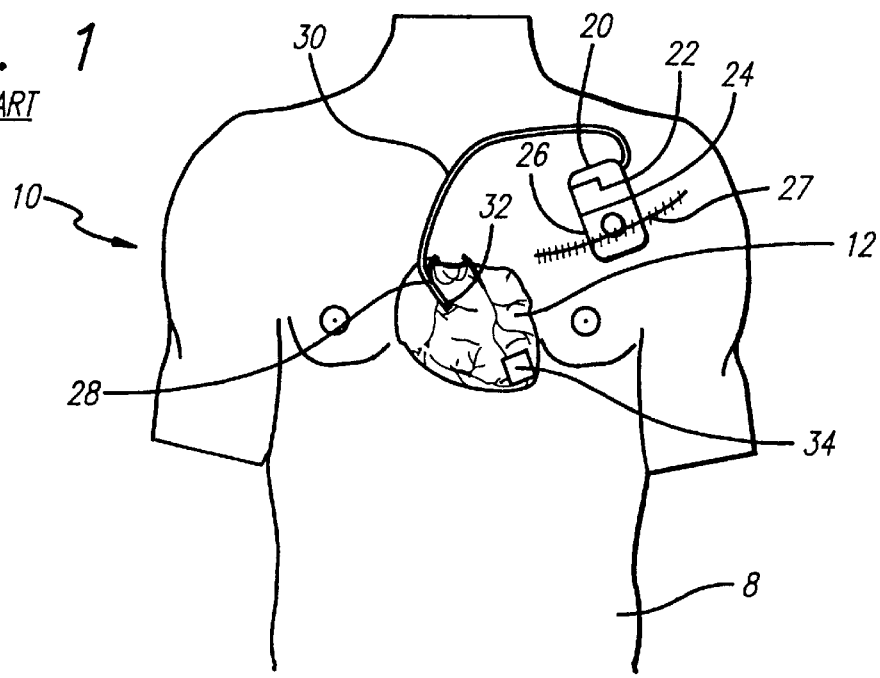
FIG. 1 is a perspective view of a conventional ICD implanted in a patient.
Figure 2:
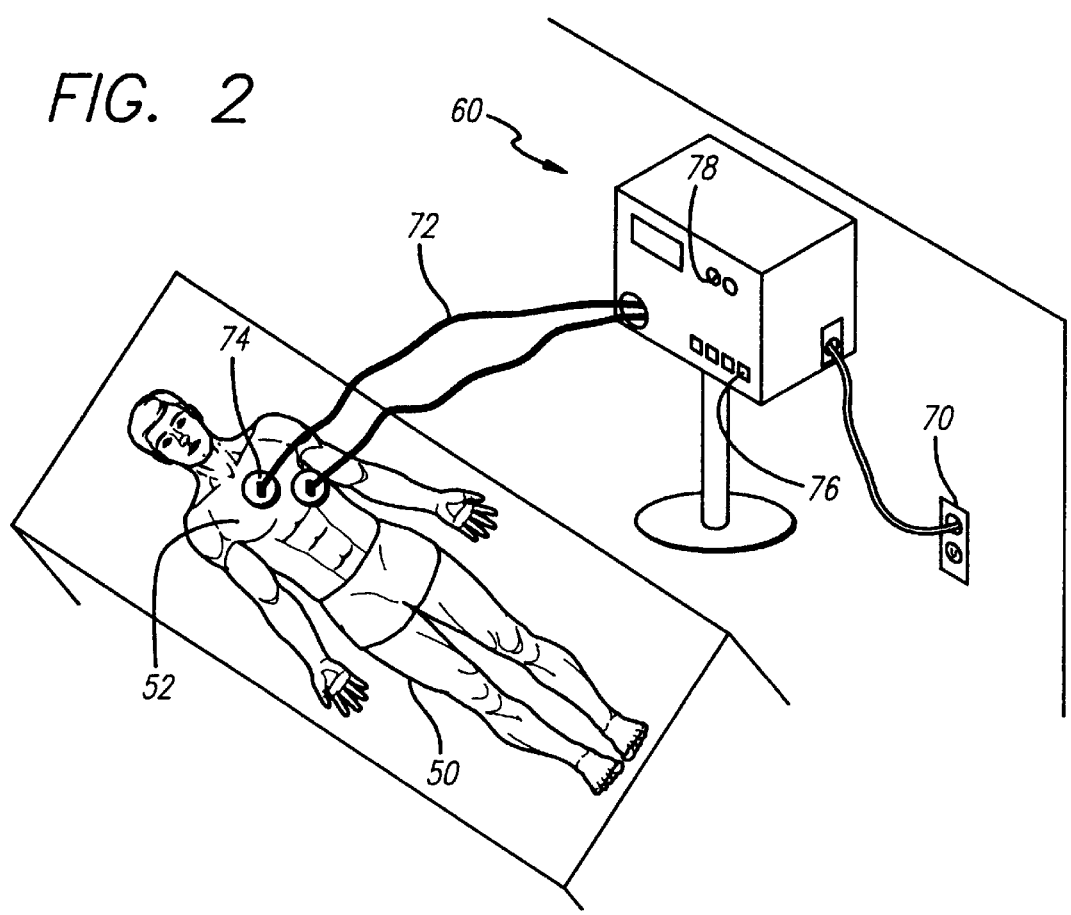
FIG. 2 is a perspective view of a conventional external defibrillator attached to a patient in the recumbent position.

The invention summarized above and defined by the enumerated claims may be better understood by referring to the following detailed description, which should be read in conjunction with the accompanying drawings. This detailed description of particular preferred embodiments, set out below to enable one to build and use those particular implementations of the invention, is not intended to limit the enumerated claims, but to serve as particular examples thereof. The particular examples set out below are the preferred specific implementations of: (1) an improved automatic implanted cardioverter defibrillator, namely, one that automatically defibrillates a heart in either VF or AF based upon an approximate entropy algorithm; and (2) an improved external defibrillator that operates on a heart in VF or AF based upon the approximate entropy algorithm. The invention, however, may also be applied to other types of arrhythmias.

Before describing the invention in further detail, it will be helpful to provide background information relating to an area of statistics known as approximate entropy ("ApEn").

I. Introduction to Approximate Entropy

More specifically, "entropy" is an area of statistics which measures data distributions. While moment statistics, such as mean and standard deviation, provides useful information relating to series of data, it cannot compare and distinguish between two series containing identical data but whose ordering of the data, or randomness, are different. Entropy statistics provides information about the randomness of a series, and enables one to distinguish between the randomness of two series. It can identify the likelihood that runs of patterns of data that are relatively close will remain relatively close on the next incremental comparisons. Entropy statistics, however, has not found wide practical utility and has been generally confined to the province of theoretical mathematicians for two reasons. First, entropy has successfully characterized only what is called the deterministic chaotic model, defined as aperiodic, seemingly random behavior in a bounded system. Such a system exhibits sensitive dependence on initial conditions, as opposed to the stochastic, or truly random, model, which is representative of many real life conditions. Second, using the entropy model, an enormous series of data is generally necessary to certify complex, deterministic settings. That is, the amount of data typically needed to achieve convergence is impractically large for real time applications, requiring supercomputers and/or huge amounts of time with which to calculate the data.

More recently, an approximate entropy algorithm has been developed in order to address the above-described practical disadvantages. This algorithm is capable of quantifying the amount of regularity in chaotic or stochastic (random) systems for practical purposes. Inherent in such an algorithm is the finding that classical entropy statistics can be modified and, with a relatively small number of data points in a time series, can provide a useful summary (approximation) of the regularity of a time series represented by a single real number. An ApEn score of 0 represents a totally periodic series, where there is no randomness; the time series is 100% predictable. At the other end of the scale, an ApEn score of 2 represents a completely stochastic, or random, and unpredictable, time series.

Following is the ApEn algorithm:

STEP 1. Form a time series of data $u(1), u(2), \ldots u(N)$. These are N raw data values from measurements equally spaced in time.

STEP 2. Fix m, an integer, and r, a positive real number. The value of m represents the length of compared runs of data, and r specifies a filtering level.

STEP 3. Form a sequence of vectors $x(1), x(2), \ldots, x(N-m+1)$ in $R^m$, real m-dimensional space, defined by $x(i)=[u(i), \ldots, u(i+m-1)]$.

STEP 4. Use the sequence $x(1), x(2), \ldots, x(N-m+1)$ to construct, for each i, $1 \leq i \leq N-m+1$, $C_i^m(r)=$(number of $x(j)$ such that $d[x(i),x(j)] \leq r)/(N-m+1)$.

We must define $d[(x(i),x(j)]$ for vectors $x(i)$ and $x(j)$. Modify the formula by defining $$d[x,x^*] = \max_a | u(a) - u^*(a)|,$$

where the $u(a)$ are the m scalar components of x. d represents the distance between the vectors $x(i)$ and $x(j)$, given by the maximum difference in their respective scalar components.

STEP 5. Next, define $$\Phi^m(r) = (N - m + 1)^{-1} \sum_{i=1}^{N-m+1} \ln C_i^m(r),$$

where ln is the natural logarithm.

Through STEP 5, the classical entropy and ApEn algorithms are identical. The next step distinguishes between classical entropy and ApEn.

STEP 6. ApEn is defined by the equation:

$$ApEn (m, r, N) = \Phi^m(r) - \Phi^{m+1}(r).$$

The ApEn formula is simple to apply and requires a relatively small amount of input data to obtain meaningful results. As the equation shows, the ApEn formula requires that three input parameters, N, m and r be set, where: N is the total number of data points to be evaluated in the time series; m is a positive integer representing the length of the compared runs within the time series (i.e. vector length), and r is a positive real number representing a noise filter. The input data for ApEn is a scalar time series, having typically between N=50 to 1000 data points. The mathematical derivation of the approximate entropy formula is further discussed in "Approximate Entropy as a Measure of System Complexity," Pincus, S. M., Proc. Natl. Acad. Sci. U.S.A., 88: 2297–2301, 1991 and is incorporated by reference.

II. Defibrillation Apparatus And Method Employing The Approximate Entropy Algorithm The present invention resides in a defibrillator apparatus and related method that defibrillates a heart based on the application of an ApEn algorithm that regulates the moment at which a regulated energy level of electric shock is delivered to the heart. The present invention advantageously identifies the moment at which the defibrillation threshold, and thus, the required energy, is at a minimum. As such, the required level of energy to accomplish defibrillation tends to be reduced.

Figure 3A:
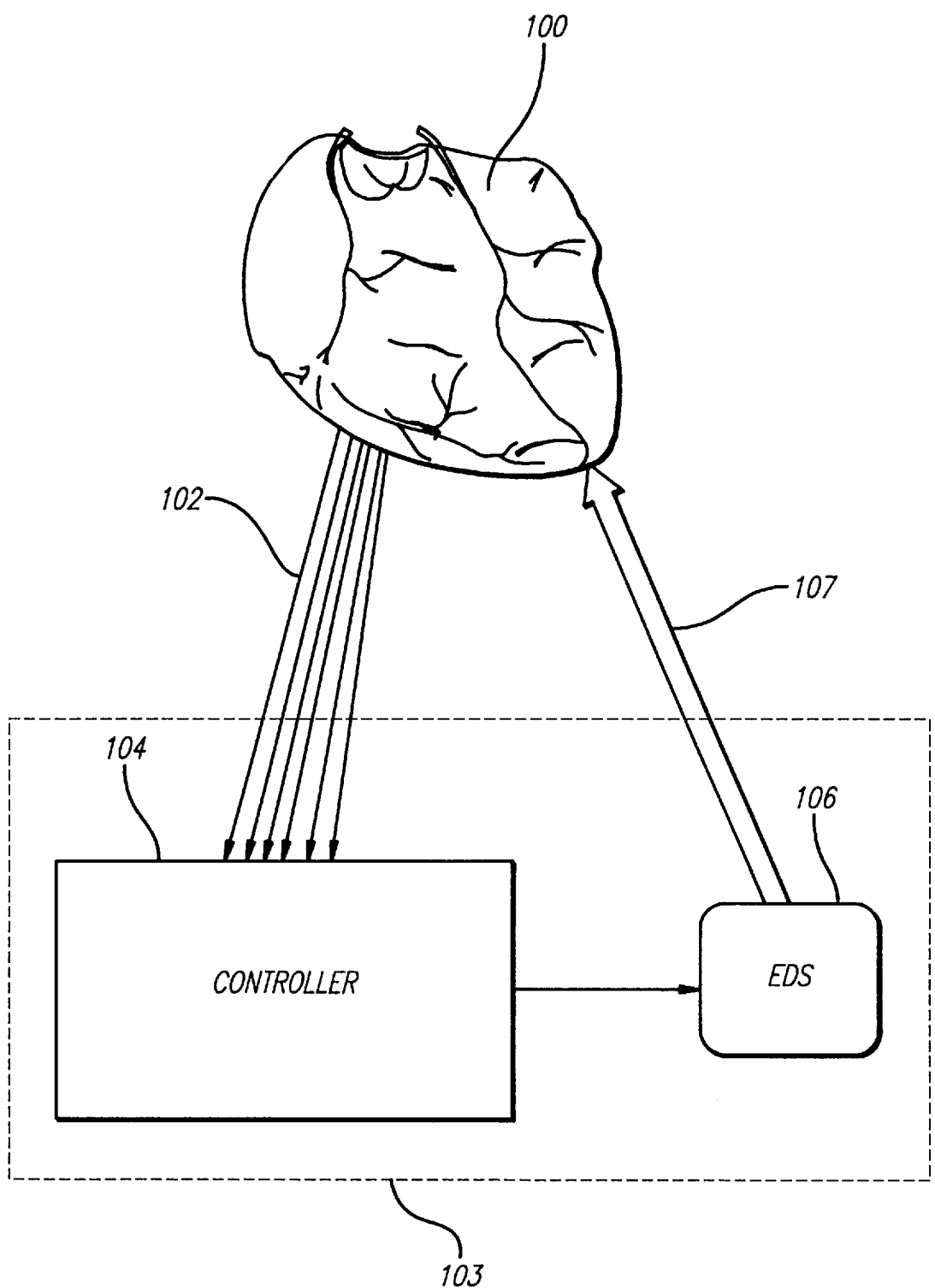
FIG. 3a is a block diagram of a defibrillator interconnected to a heart shown in perspective view.

With reference now to the exemplary drawings, and particularly to FIG. 3a, there is shown a defibrillator 103 having a controller 104 and energy delivery system ("EDS") 106 that is interconnected to a patient's heart 100 via sensors 102 and therapy leads 107 and are situated on the surface of the heart or within the heart. Any suitable defibrillating sensors may be employed. Alternatively, a single sensor having multiple sensing poles may be employed. The sensors, or poles of a single sensor, are further advantageously deployed in a quantity sufficient to detect and transmit any appropriate amount of data indicative of the heart rhythm. To that end, they preferably, but not necessarily, have multiple electrodes associated with the heart and transmit data in parallel to the controller 104 contained within the defibrillator 103. The controller activates the EDS also contained within the defibrillator which then delivers a defibrillating shock to the heart via therapy leads 107.

As shown in FIG. 3b, the controller 104 includes a processor 108 and a storage unit 109, which together function to selectively activate the energy delivery system 106 in response to an approximate entropy score derived by the processor 108 from the data. More particularly, the processor 108 includes a fibrillation detector 110 that detects, from the data provided by the sensors 102, the presence of fibrillation. Any conventional method of fibrillation detection, such as that shown in step 202 of FIG. 4, and described below, may be employed. The processor also includes a data manipulator 114 which processes the in-parallel input data from the sensors into a single number. The manipulation shown is an averaging function but other functions may also be used. The processor further includes an ApEn computer 120, an ApEn comparator 124 and an EDS activator 126. The storage unit 109 includes a data register 112 which receives the in-parallel data provided by the sensors 102. This may be a parallel-in, parallel-out register or other suitable temporary data storage component. The unit also contains a time series register 116 for temporarily storing a series of data representative of the fibrillating heart over an equally-spaced time period. The storage unit 109 further contains an ApEn algorithm-storing memory 118 and an ApEn threshold value memory 122. These memories can be read only memories ("ROM's") or any of a variety of conventional programmable ROM's, such as EEPROM's. It will be appreciated that the programming of software, such as the Pincus ApEn algorithm, into a memory such as the ApEn algorithm memory 118 is performed in a well understood manner.

In operation, when the fibrillation detector 110 detects the presence of a fibrillation, it enables the data manipulator 114 to receive the in-parallel data from the data register 112. The manipulator 114 averages the data and outputs a single real number representative of the state of the heart at a given instant. This number is then temporarily stored in a time series register 116. The time series register has the capacity to store at least N addressable numbers, the total number of data points in the time series. These steps are repeated at equal time intervals. This creates a scalar time series of data from 1 to N, stored in the time series register, representing the state of the heart over the time series. The ApEn computer 120 receives the time series data from the register 116 and applies the algorithm, or program, supplied by the memory 118 to the scalar time series of data to compute an approximate entropy score. Next, the comparator 124 compares the computed approximate entropy score of the time series to a threshold approximate entropy value, or range of values, stored in the ApEn threshold value memory 122. If the proper condition, or predetermined relation, is met, as described in detail below and in FIG. 4, the EDS activator 126 will signal the EDS to deliver a defibrillating shock to the heart.

The EDS 106 includes well known types of components used in existing shock generators; namely, a capacitor, battery, and pulse generating circuitry (not shown). Nevertheless, in accordance with the invention, the EDS 106 uses a smaller capacitor and smaller battery, thereby reducing the weight of the defibrillator and tending to extend its useful life. In particular, the defibrillator of the present invention needs only to provide a smaller fraction of the energy that would otherwise be required to defibrillate a given patient. It thus uses a capacitor relatively, significantly smaller than capacitors designed in conventional defibrillators. This tends to result in two important advantages for ICD's: (1) the lower energy requirement translates into a reduced power drain on the charging batteries, resulting in the ability to design in smaller batteries to accomplish the same charging job as before. Moreover, batteries of a size presently used in defibrillators tend to enjoy a longer life, thereby extending the usable life of the ICD; and (2) the smaller EDS 106 having the smaller capacitor and battery results in a significantly smaller control box and an attendant decrease in discomfort for the patient within whom it is implanted.

The above advantages also foster other advantages, namely a reduction in the shock energy level that would otherwise be necessary and an attendant lessening of the pain and discomfort that would otherwise be experienced.

Figure 4:
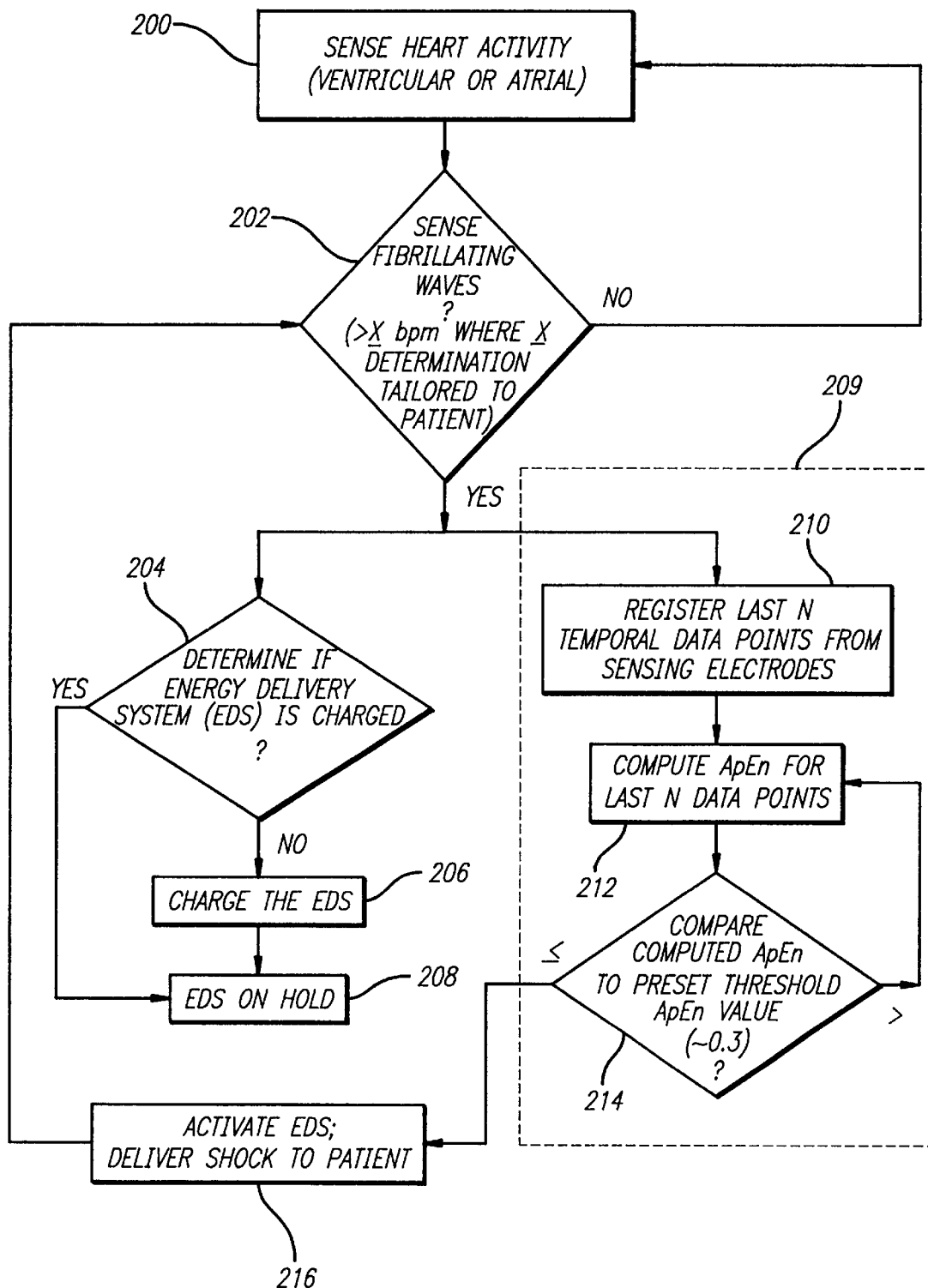
FIG. 4 is a flowchart illustrating steps performed in the preferred method of the invention.

FIG. 4, in flow chart form, depicts steps taken of a method of defibrillation in accordance with the invention, which is particularly applicable to ventricular or atrial defibrillation. In an initial step 200, the ventricular or atrial rate of the heart is sensed. Step 202 determines whether an abnormal heart condition is present; i.e. whether a fibrillation wave is sensed. This is conventionally accomplished by determining whether the ventricular or atrial rate exceeds a preset value, x, such as 240 beats per minute ("bpm"). This value is typically tailored to the patient, as is well known in the art. If an abnormal condition is not sensed, the device loops back to step 200 to repeatedly sense for the presence of an abnormal condition.

When an abnormal condition is sensed, two steps occur. In step 204, the EDS is checked to determine whether it is charged and ready to delivery a shock when called upon. If it is not, the EDS is charged in step 206 and enters into a standby mode, depicted by step 208. Concurrently, the on-line ApEn routine 209 commences. Specifically, in step 210, the last N temporal data points, derived from the sensed data, are registered and comprise the first time series of data, as described above in the detailed description of FIG. 3b. In the preferred embodiment, the time series is comprised of 50 data points equally spaced in time, i.e. N=50. A time series of 50 data points is an experimentally determined quantity of data that achieves a fair balance of reliability and speed. On the one hand, 50 data points has been determined to be sufficient for reliable output from the ApEn calculation, which is the key ingredient to effective and safe low-energy defibrillation. On the other hand, a 50 point series of data is small enough to facilitate fast, on-line processing with state-of the-art processors. Speed, of course, is inherently important in the art of defibrillation, and particularly in ventricular defibrillation, as the difference between death from cardiac arrest and life is often a matter of minutes. It is understood that N is not limited to this number for effective ApEn defibrillation and will likely change with the ever-increasing computational speeds of processors.

In the subsequent step 212, the ApEn of the first time series is computed according to the ApEn algorithm. It is understood that this is but one expression of the ApEn algorithm as applied to defibrillation, and that implementation of algorithms is performed in a well known manner. In one preferred embodiment, the computational speed of the ApEn of each time series is approximately 0.5 seconds.

In the next conditional step 214, the ApEn of the first time series is compared to at least one preset ApEn threshold value. The EDS is activated when the ApEn score has a predetermined relation with respect to the preset ApEn threshold value or values. In one preferred embodiment, the ApEn threshold value is 0.3. This number is based upon ApEn input variables of vector, m=2, filter value, r=25% of the standard deviation of the input values, and a time series having N=50 input values. If the computed ApEn score is greater than the threshold value, then the pattern of fibrillation is not stable (regular) enough for successful low-level defibrillation and the process repeats itself for a second time series of data with a return to step 210. This routine is repeated until the computed ApEn value is less than the ApEn threshold value. When this occurs, the optimum condition for low level defibrillation is met and the charged EDS is activated in step 216 and delivers a low level shock to the heart.

In another preferred embodiment, step 214 is modified so that the computed ApEn value is compared to two ApEn threshold values—a lower threshold and an upper threshold. In this embodiment, if the ApEn value is either below the lower threshold or above the upper threshold the EDS is activated to provide a low level defibrillating shock.

After the shock is delivered, the process returns to step 202 for evaluation. Thus, if the defibrillating shock was successful and normal sinus rhythm is returned, step 202 responds negatively to the abnormal condition inquiry, and the step 200-to step 202-back to step 200 loop will continue indefinitely, until the next episode of fibrillation is sensed. However, if the shock was not successful in converting the heart to normal sinus rhythm, then the ApEn routine 209 and the EDS charging routine, steps 204 to 208, will once again be invoked. This entire process will continue until one of the following conditions are met: (a) a low level shock finally succeeds in defibrillating the patient; (b) a preset limit to the number of shocks delivered is reached (not shown); or (c) a preset duration of time delay since the onset of fibrillation is reached. If either of the last two conditions occur, the defibrillator is instructed to revert to a conventional defibrillation mode. It is appreciated that the preset limit or duration for atrial defibrillation may be larger than for ventricular defibrillation because AF is not immediately life threatening as is VF.

Underlying the present invention is the understanding that the conventional assumption that the fibrillation mechanism is totally random is incorrect. Using detailed computer mapping techniques to track the activity of fibrillating hearts we discovered that the fibrillation paradigm is not totally random but rather exhibits chaotic behavior. In fact, there exist patterns of regularity in the "abnormal" activation patterns of a fibrillating heart.

Moreover, it is evident from the foregoing that analysis of these patterns of fibrillation can be valuable in treating this potentially deadly condition. Specifically, at moments of relative regularity of heart activation during a fibrillation episode (low approximate entropy score), the fibrillation threshold is reduced. That is, converting a defibrillating heart to normal sinus rhythm can be achieved with the application of an electric shock having an energy level significantly lower than previously possible. The same phenomenon (reduction in the defibrillation threshold) has been found to occur when the electrical activity of the heart displays a relatively high degree of randomness (high approximate entropy score).

The ApEn algorithm enables identification of these moments of relative regularity or relative irregularity. Specifically, the moment a chaotic fibrillation episode manifests a relatively low or high ApEn value the defibrillation threshold is significantly reduced. An example of an experiment that was conducted to apply the theory is detailed below. It will be understood, however, that the particular tests, including the number of electrodes mentioned, are set forth for the purpose of providing an example to amplify the foregoing description of the invention.

1. Testing

VF was induced in swine hearts by applying bi-phasic electrical shocks across the myocardium. 500 electrodes were placed on the heart tissue to sense and record electrical activity. This activity was repeatedly recorded as 500 distinct channels using computerized activation mapping techniques at short intervals. At various moments during the fibrillation episodes, defibrillating shocks of varying intensities were applied.

2. Results

Table 1 shows the results of one series of such tests:

TABLE 1

| Test Number | ApEn | Energy Applied | Defibrillation Outcome |
| --- | --- | --- | --- |
| 1 | 0.446 | 2.0 joules | Failure |
|   | 0.271 | 1.7 joules | Success |
| 2 | 0.470 | 1.5 joules | Failure |
|   | 0.274 | 1.4 joules | Success |
| 3 | 0.249 | 1.3 joules | Failure |
|   | 0.236 | 1.3 joules | Success |
| 4 | 0.616 | 1.2 joules | Success |
|   | 0.311 | 1.3 joules | Failure |

In test numbers 1 through 3 defibrillation was successful only when the ApEn was lower than 0.3. In test 4 defibrillation was successful when the ApEn was above 0.6. Additional testing has supported these findings.

It will be observed that the present invention also has application to external defibrillators. Among other things, it tends to relatively, significantly reduce the shock energy otherwise needed for successful conversion and to lessen the severe pain historically associated with the defibrillation shock.

From the foregoing description, it should be apparent that the present invention provides a method and apparatus for low energy defibrillation which times the delivery of the shock to the fibrillating heart to coincide with the moment that the defibrillation threshold is at a minimum.

Although the invention has been described in detail with reference only to the presently preferred devices and method, those of ordinary skill in the art will appreciate that various modifications can be made without departing from the invention. Accordingly, the invention is defined only by the following claims.

We claim:

1. An apparatus for defibrillating a heart, comprising:
   a first sensor associated with the heart, the sensor being configured to detect a heart rhythm and transmit data indicative of the rhythm;
   an energy delivery system associated with the heart for delivery to the heart an electric shock of a predetermined energy level; and
   a controller responsive to the sensor that selectively activates the energy delivery system in response to an approximate entropy score derived by the controller from the data.

2. The apparatus of claim 1, wherein the energy delivery system comprises:
   an electric shock generator; and
   at least one therapy electrode connected to the electric shock generator.

3. The apparatus of claim 2, wherein the apparatus is an external defibrillator.

4. The apparatus of claim 2, wherein the apparatus is an implantable defibrillator.

5. The apparatus of claim 4, wherein the first sensor is associated with a ventricle of the heart.

6. The apparatus of claim 4, wherein the first sensor is associated with an atrium of the heart.

7. The apparatus of claim 4, wherein the first sensor and therapy electrode are integral.

8. The apparatus of claim 4, wherein the first sensor includes multiple sensing poles.

9. The apparatus of claim 1, further including a second sensor associated with the heart and being configured to detect a heart rhythm and transmit data indicative of the rhythm.

10. The apparatus of claim 1, wherein the controller is adapted to repeatedly compute from the data substantially equally spaced in time discrete data points comprising a scalar time series.

11. The apparatus of claim 10, wherein the controller derives the approximate entropy score from the scalar time series.

12. The apparatus of claim 11 wherein the approximate entropy score is defined by the equation:

$$ApEn(m,r,N) = \phi^m(r) - \phi^{m+1}(r).$$

13. The apparatus of claim 12 wherein the approximate entropy score ranges from 0 to 2.

14. The apparatus of claim 13 wherein the controller is adapted to: (a) compare the approximate entropy score to a first preset approximate entropy threshold value stored in a memory of the controller; and (b) selectively activate the energy delivery system when the approximate entropy score has a predetermined relation with respect to the first preset approximate entropy threshold value.

15. The apparatus of claim 14 wherein the predetermined relation arises when the approximate entropy score is less than the first preset approximate entropy threshold value.

16. The apparatus of claim 15 wherein the first preset approximate entropy threshold value is approximately 0.3 when N=500, m=2 and r=approximately 25% of the standard deviation of the scalar time series.

17. The apparatus of claim 13 wherein the controller is adapted to: (a) compare the approximate entropy score to a first preset approximate entropy threshold value and a second preset approximate entropy threshold value stored in a memory of the controller; and (b) selectively activate the energy delivery system when the approximate entropy score is either less than the first preset approximate entropy threshold value or greater than the second preset approximate entropy threshold value.

18. The apparatus of claim 1 wherein the predetermined energy level is substantially less than about 10 joules.

19. The apparatus of claim 18 wherein the preset energy level is substantially less than about 5 joules.

20. A defibrillator for a heart, comprising:
a sensor associated with the heart, the sensor being configured to detect a heart arrhythmia and transmit data indicative of the arrhythmia;
an energy delivery system associated with the heart for delivery to the heart an electric shock of a predetermined energy level; and
a controller including;
  a sensor data processor receptive of the data to repeatedly compute a plurality of data points substantially equally spaced in time;
  an approximate entropy processor to repeatedly compute an approximate entropy score from the data points;
  a comparator to compare the approximate entropy score to at least one preset approximate entropy threshold value stored in a memory of the controller; and
  an energy delivery system activator to monitor the output of the comparator and to activate the energy delivery system when the approximate entropy score has at least one predetermined relation with respect to the at least one preset approximate entropy threshold value, thereby defibrillating the heart.

21. A defibrillator for a heart, comprising:
an energy delivery system associated with the heart that delivers to the heart an electric shock of a predetermined energy level; and
a controller that receives data indicative of the rhythm of the heart and that selectively activates the energy delivery system in response to an approximate entropy score derived by the controller from the data.

22. The defibrillator of claim 21, wherein the energy delivery system comprises:
an electric shock generator; and
at least one therapy electrode connected to the electric shock generator.

23. The defibrillator of claim 22, wherein the defibrillator is external.

24. The defibrillator of claim 22, wherein the defibrillator is implanted.

25. The defibrillator of claim 21, wherein the controller: (a) is adapted to repeatedly compute from the data substantially equally spaced in time data points comprising a scalar time series; and (b) derives the approximate entropy score from the scalar time series.

26. The defibrillator of claim 25, wherein the approximate entropy score is defined by the equation:

$$ApEn(m,r,N) = \phi^m(r) - \phi^{m+1}(r).$$

27. The defibrillator of claim 26, wherein the approximate entropy score ranges from 0 to 2.

28. The defibrillator of claim 27, wherein the controller is adapted to: (a) compare the approximate entropy score to at least one preset approximate entropy threshold value stored in a memory of the controller; and (b) selectively activate the energy delivery system when the approximate entropy score has a predetermined relation with respect to the at least one preset approximate entropy threshold value.

29. The defibrillator of claim 21, wherein the preset energy level is substantially less than about 10 joules.

30. The defibrillator of claim 29, wherein the preset energy level is substantially less than about 5 joules.

31. A defibrillator for a heart, comprising:
means for sensing an arrhythmia and for generating data indicative of the arrhythmia;
means associated with the heart for providing at least one electric shock to the heart; and
means for selectively activating the means for providing the at least one electric shock based upon an approximate entropy score.

32. The defibrillator of claim 31, wherein the activating means further includes means for determining the approximate entropy score based on the data.

33. The defibrillator of claim 32, wherein the selectively activating means further includes means for comparing the approximate entropy score to at least one preset approximate entropy threshold value and for activating the shock providing means when the approximate entropy score has a predetermined relation with respect to the at least one preset approximate entropy threshold value.

34. A method for defibrillating a heart, comprising:
sensing a heart arrhythmia and generating data indicative of the arrhythmia;
determining an approximate entropy score based on the data;

selectively activating an energy delivery system to deliver a defibrillating shock to the heart based on the approximate entropy score.

35. The method as defined in claim 34, wherein the method further includes comparing the approximate entropy score to at least one preset approximate entropy threshold value.

36. The method as defined in claim 35, wherein the energy delivery system is activated when the approximate entropy score has a predetermined relation with respect to the preset approximate entropy threshold value.

37. The method as defined in claim 34, wherein the heart arrhythmia sensed is ventricular fibrillation.

38. The method as defined in claim 34, wherein the heart arrhythmia sensed is atrial fibrillation.

* * * * *

UNITED STATES PATENT AND TRADEMARK OFFICE
CERTIFICATE OF CORRECTION

PATENT NO. : 5,817,132  Page 1 of 1
DATED : October 6, 1998
INVENTOR(S) : Hrayr S. Karagueuzian and Peng-Sheng Chen It is certified that error appears in the above-identified patent and that said Letters Patent is hereby corrected as shown below:

Title page,
Item [56], References Cited, U.S. PATENT DOCUMENTS, please add the following:
-- 3,942,536   3/1976       Mirowski et al.
   4,316,472   2/1982       Mirowski et al.
   4,407,288   10/1983      Langer et al.
   4,572,191   2/1986       Mirowski et al.
   4,830,006   5/1989       Haluska et al.
   5,555,889   9/1996       Karagueuzian et al. --; and
insert -- OTHER PUBLICATIONS
*Approximate Entropy as a Measure of System Complexity,*
S. M. Pincus, Proc. Natl. Acad. Sci. USA, Vol. 88, pp. 2297-2301 (1991)

*Quantification of Hormone Pulsatility Via an Approximate Entropy Algorithm,*
S. M. Pincus, Am. Phys. Society, pp. E741-E754 (1992)

*A Regularity Statistic for Medical Data Analysis,*
S. M. Pincus et al., J. Clin, Monit., Vol. 7, No. 4, pp. 335-345 (1991) --

Signed and Sealed this

Tenth Day of February, 2004

JON W. DUDAS
*Acting Director of the United States Patent and Trademark Office*